US00PP13528P2

(12) United States Plant Patent
Gerdts et al.

(10) Patent No.: US PP13,528 P2
(45) Date of Patent: Jan. 28, 2003

(54) PEACH TREE, NAMED 'BURPEACHELEVEN'

(75) Inventors: Timothy J. Gerdts, Kingburg, CA (US); John K. Slaughter, Clovis, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 10/044,369

(22) Filed: Jan. 11, 2002

(51) Int. Cl.[7] ..... A01H 5/00

(52) U.S. Cl. ..... Plt./197

(58) Field of Search ..... Plt./197

*Primary Examiner*—Bruce R. Campell
*Assistant Examiner*—Susan B. McCormick
(74) *Attorney, Agent, or Firm*—Wells St. John P.S.

(57) ABSTRACT

A new and distinct variety of peach tree (*Prunus persica*), denominated varietally as 'Burpeacheleven', and which produces an attractively colored yellow-fleshed, sub-acid clingstone peach which is mature for harvesting and shipment approximately August 22 to August 31 under ecological conditions prevailing in the San Joaquin Valley of Central California.

1 Drawing Sheet

BACKGROUND OF THE NEW VARIETY

Botanical classification: *Prunus persica.*

Variety denomination: 'Burpeacheleven'.

The present invention relates to a new, novel and distinct variety of peach tree, *Prunus persica*, which has been denominated varietally as 'Burpeacheleven'. The present variety of peach tree resulted from an on-going program of fruit and nut tree breeding. The purpose of this program is to improve the commercial quality of deciduous fruit and nut varieties and rootstocks by creating and releasing promising selections of prunus, malus and regia species. To this end we make both controlled and hybrid cross pollinations each year in order to produce seedling populations from which improved progenies are evaluated and selected.

The seedling 'Burpeacheleven' was originated by us from a population of seedlings grown in our experimental orchards located near Fowler, Calif. The seedlings, grown on their own roots, were the result of a controlled cross of an unnamed peach tree which was used as the pollen parent and the peach tree 'A48-70', (unpatented) which was used as the seed parent. One seedling, which is the present variety, exhibited especially desirable characteristics and was marked for subsequent observation. After the 1997 season, the new present variety was selected for advanced evaluation and repropagation.

ASEXUAL REPRODUCTION

Asexual reproduction of the new and distinct variety of peach tree was accomplished by budding to 'Nemaguard' Rootstock (non-patented). This was performed by us in our experimental orchard located near Fowler, Calif. Subsequent evaluations have shown those asexual reproductions run true to the original tree. All characteristics of the original tree and its fruit were established and appear to be transmitted through succeeding asexual propagations.

SUMMARY OF THE VARIETY

'Burpeacheleven' is a new and distinct variety of peach tree, which is of large size, and which has vigorous growth, and which further is a regular and productive bearer of large, firm, sub-acid yellow flesh, clingstone fruit with good flavor and eating quality. The tree has a medium-high chilling requirement of approximately 750 hours. The tree also produces relatively uniformly sized fruit throughout the tree with a high degree of red skin coloration, and firm flesh. The fruit appears to have good handling and shipping quality. Still further, the 'Burpeacheleven' peach tree bears fruit that is ripe for commercial harvesting and shipment on approximately August 22 to August 31. In comparison to the seed parent 'A48-70' Peach, ( un-patented ) the new variety ripens 15 or more days later.

BRIEF DESCRIPTION OF THE DRAWING

The accompanying drawing which is provided is a color photograph of the present variety. It depicts two whole mature fruit, and one fruit dissected in the equatorial plane exposing the flesh and the pit. Additionally, a characteristic twig bearing typical leaves is shown. The external coloration of the fruit is shown, and which is sufficiently matured for harvesting and shipment. The colors are as nearly true as is reasonably possible in a color representation of this type. Due to chemical development, processing and printing, the leaves and fruit depicted in this photograph may or may not be accurate when compared to the actual specimen. For this reason, future color references should be made to the color plates (Royal Horticultural Society) and descriptions provided.

DETAILED DESCRIPTION

Referring more specifically to the pomological details of this new and distinct variety of peach tree, the following has been observed during the fourth fruiting season under the ecological conditions prevailing at orchards located near the town of Fowler, county of Fresno, state of California. All major color code designations are by reference to The R.H.S. Colour Chart (Fourth Edition) provided by The Royal Horticultural Society of Great Britain.

Tree:

*Size.*—Generally. — Considered medium large as compared to other common commercial peach cultivars ripening in the late season of maturity. The tree of the present variety was pruned to a height of approximately 314.8 cm to 386.7 cm at maturity.

*Vigor.*—Moderately vigorous. The present variety grew from about 141.0 cm to 195.7 cm in height during the first growing season. The variety was pruned to a height of approximately 106.7 cm during the first dormant season and primary scaffolds were then selected for the desired tree structure.

*Productivity.*—Productive. Fruit set varies from 2.0 to several times more than the desired crop load. Fruit set is spaced by thinning to develop into the desired market sized fruit. Number of fruit set varies with climatic conditions and cultural practices during the bloom period and is therefore not distinctive of the variety.

*Bearer.*—Regular. Fruit set has been heavy, and thinning was necessary during the past 4 years.

*Form.*—Upright, and pruned to a vase shape.

*Density.*—Medium dense. It has been discovered that pruning the branches from the center of the tree to obtain a resulting vase shape allows for air movement and appropriate amounts of sunlight to enhance fruit color and renewal of fruiting wood throughout the tree.

*Hardiness.*—The present tree was grown and evaluated in USDA Hardiness Zone 9. Winter chilling requirements are approximately 750 hours below 7.0 degrees C. The present variety appears to be hardy under typical Central San Joaquin Valley conditions.

Trunk:

*Diameter.*—Approximately 15.0 cm in diameter when measured at a distance of approximately 15.24 cm above the soil level, at the end of the fourth growing season.

*Bark Texture.*—Considered moderately rough, with numerous folds of papery scarfskin being present.

*Lenticels.*—Numerous flat, oval lenticels are present. The lenticels range in size from approximately 3.0 to 6.0 millimeters in width, and from 1.0 to 2.0 millimeters in height.

*Lenticel color.*—Considered an Orange Brown, (RHS Greyed-Orange N170 A).

*Bark coloration.*—Variable, but it is generally considered to be grey-brown, (RHS Grey-Brown Group N199 B).

Branches:

*Size.*—Considered medium for the variety.

*Diameter.*—Average as compared to other varieties. The branches have a diameter of about 6.5 centimeters when measured during the fourth year after grafting.

*Surface texture.*—Average, and appearing furrowed on wood which is several years old.

*Crotch angles.*—Primary branches are considered variable between about 45 to 49 degrees from the horizontal axis. This characteristic is not considered distinctive of the variety, however.

*Current season shoots.*—Surface texture — Substantially glabrous.

*Internode length.*—Approximately 2.3 to 2.4 cm.

*Color of mature branches.*—Medium brown, (RHS Grey Brown Group N199C).

*Current seasons shoots.*—Color. — Light green, (RHS Yellow Green Group 144 A). The color of new shoot tips is considered a bright and shiny green (RHS Green Group 141D).

Leaves:

*Size.*—Considered medium large for the species. Leaf measurements have been taken from vigorous, upright, current-season growth at approximately mid-shoot.

*Leaf length.*—Approximately 165 to 185 millimeters.

*Leaf width.*—Approximately 40 to 45 millimeters.

*Leaf base shape.*—Slightly oblique relative to the leaf longitudinal axis.

*Leaf form.*—Lancelolate.

*Leaf tip form.*—Acuminate.

*Leaf color.*—Dark green, (approximately RHS Green Group 141 B).

*Leaf texture.*—Glabrous.

*Lower surface.*—Medium green, (RHS Green Group 143 B).

*Leaf venation.*—Pinnately veined.

*Mid-vein.*—Color. — Light yellow green, (RHS Yellow Green Group 145 C).

*Leaf margins.*—Slightly undulating. Form. — Considered crenate, occasionally doubly crenate. Uniformity. — Considered generally uniform.

*Leaf petioles.*—Size. — Considered long. Length. — about 11.0 to about 15.0 mm. Diameter. — about 1.5 to about 2.5 mm. Color. — Pale green, (RHS Yellow Green Group 144 D).

*Leaf glands.*—Size. — About 1.0 mm in height, and about 1.0 to 2.0 mm in width. Number. — Generally one per side, occasionally two per side. Type. — Reniform, and considered reasonably unappressed to the petiole margin. Color. — Greenish brown, (RHS Yellow Green Group146 B).

*Leaf stipules.*—Size. — Medium large for the variety. Number. — Typically 2 per leaf bud and up to 6 per shoot tip. Form. — Lanceolate in form, and having a serrated margin. Color. — Green, (RHS Green Group 132 A) when young, but graduating to a brown color, (RHS Grey Orange group 177 A) with advancing senescence. The stipules are considered to be early deciduous.

Flowers:

*Flower buds.*—Generally — The floral buds, depending on stage of development, are approximately 8.0 millimeters wide; and about 12.0 millimeters long; conic in form; and slightly appressed relative to the bearing shoot.

*Flower buds.*—Color — The bud scales are reddish-brown, (approximately RHS Greyed Purple Group 183 A). The buds are considered hardy under typical central San Joaquin Valley climatic conditions.

*Hardiness.*—No winter injury has been noted during the last several years of evaluation in the central San Joaquin Valley. The current variety has not been intentionally subjected to drought or heat stress and therefore this information is not available.

*Date of first bloom.*—Feb. 27, 2000.

*Blooming time.*—Considered mid-season in comparison to other commercial peach cultivars grown in the central San Joaquin Valley. Date of full bloom was observed on Mar. 4, 2000. The date of bloom varies slightly with climatic conditions and cultural practices.

*Duration of bloom.*—Approximately 8 days. Varies slightly with climatic conditions.

*Flower type.*—The variety is considered to have a non-showy type flower.

*Flower size.*—Flower diameter at full bloom is approximately 32.0 to 35.0 millimeters.

*Bloom quantity.*—Considered abundant.

*Flower bud frequency.*—Normally 1 to 2 appear per node.

*Petal size.*—Generally — Considered small for the species. Length. — Approximately 14.0 to 16.0 millimeters. Width. — Approximately 9.0 to 12.0 millimeters.

*Petal form.*—Broadly ovate.

*Petal count.*—Nearly always 5.

*Petal texture.*—Glabrous.

*Petal color.*—Light pink when young, (RHS Red Purple Group 63 A), and darkening with advancing senescence and exposure to sunlight to a medium to dark pink, (RHS Red Purple Group 61 B).

*Fragrance.*—Slight.

*Petal claw.*—Form. — The claw is considered truncate, and has a medium-small size when compared to other varieties. Length. — Approximately 6.0 to 8.0 millimeters. Width. — Approximately 4.0 to 6.0 millimeters.

*Petal margins.*—Generally considered variable, from nearly smooth, to moderately undulate and ruffled, especially apically.

*Petal apex.*—Generally — The petal apices appear rounded.

*Flower pedicel.*—Length. — Considered medium-long, and having an average length of approximately 3.0 to 4.0 millimeters. Diameter. — Considered average, approximately 2.0 millimeters. Color. — A medium brown, (RHS Grey Brown Group N199 D).

*Floral nectaries.*—Color. — A Dull orange-gold, (RHS Greyed Orange Group 169 B).

*Calyx.*—Surface texture. — Generally glabrous. Color. — A dull red, (approximately RHS Greyed Purple Group 183 A).

*Sepals.*—Surface texture. — The surface has a short, fine pubescent texture. Size. — Average, and ovate in form. Color. — A dull red, (approximately RHS Greyed-Red Group 178 A).

*Anthers.*—Generally. — Average to above average in length. Color. — Red to reddish-orange dorsally, (approximately RHS Greyed Red Group 179 A).

*Pollen production.*—Pollen is abundant, and has a yellow color, (approximately RHS Yellow Orange Group 17 B).

*Filaments.*—Size. — Variable in length, approximately 11.0 to 13.0 millimeters in length. Color. — Considered white to a pinkish-white, (RHS Red Purple Group 62 D).

*Pistil.*—Number. Usually 1, rarely 2. Generally. — Average in size. Length. — Approximately 16.0 to 19.0 millimeters including the ovary. Color. — Considered a very pale green, (approximately RHS Yellow Green Group 151 D). Surface texture. — The variety has a long pubescent pistil.

Fruit:

*Maturity when described.*—Firm ripe condition (shipping ripe). Date of first picking. — Aug. 22, 2000. Date of last picking. — Aug. 31, 2000. The date of harvest varies slightly with climatic conditions.

*Size.*—Generally — Considered large, and uniform.

*Average cheek diameter.*—Approximately 75.0 to 77.0 millimeters.

*Average axial diameter.*—Approximately 73.0 to 75.0 millimeters.

*Typical weight.*—Approximately 255.0 grams. This is highly dependent upon cultural practices and therefore is not distinctive of the variety.

*Fruit form.*—Generally — Moderately oblate. The fruit is generally uniform in symmetry.

*Fruit suture.*—Shallow, and extending from the base to the apex. No apparent callusing or stitching exists along the suture line.

*Suture.*—Color — This appears to be a yellow to golden yellow background, (approximately RHS Orange Group 29 A), and occasionally having some red coloration, (approximately RHS Orange-Red Group N34 B).

*Ventral surface.*—Form — Slightly indented.

*Apex.*—Rounded.

*Base.*—Retuse.

*Stem cavity.*—Rounded to slightly elongated in the suture plane. Average depth of the stem cavity is about 1.95 cm. Average width is about 2.51 cm.

*Fruit skin.*—Thickness. — Considered medium in thickness, and tenacious to the flesh. Texture. — Short, fine , and pubescent. Taste. — Non-astringent. Tendency to crack. — None observed.

*Color.*—Blush color. — This red blush color is variable from a reddish orange, (approximately RHS Red Orange Group N34 B) to a dark red, (approximately RHS Red Group 43 B). Blush color ranges from about 70% to 90% of the fruit surface depending upon the sunlight exposure and prevailing growing conditions. Ground color. — Yellow orange, (approximately RHS Yellow Orange Group 20 A).

*Fruit stem.*—Medium in length, approximately 7.0 to 8.0 millimeters. Diameter. — Approximately 2.0 to 3.0 millimeters. Color. — Pale yellow-green, (approximately RHS Yellow Green Group 144 D).

*Flesh.*—Ripens. — Evenly. Texture. — Firm, and dense. Fibers. — Few, small, and tender. Aroma. — Very slight. Eating quality. — Very good. Flavor. — Considered sweet and sub-acidic. The flavor is considered both pleasant and balanced. Juice. — Moderate. Brix. — About 14.0 degrees. This characteristic varies slightly with the number of fruit per tree, prevailing cultural practices, and the surrounding climatic conditions. Flesh color. — Pale yellow, (approximately RHS Yellow-Orange Group 21 A).

Stone:

*Type.*—Clingstone.

*Size.*—Considered medium for the variety.

*Length.*—Average, about 22.0 to about 24.0 millimeters.

*Width.*—Average, about 21.0 to about 22.0 millimeters.

*Diameter.*—Average, about 19.0 to 20.0 millimeters.

*Form.*—Obovoid.

*Base.*—The stone is usually rounded, however it may vary occasionally from rounded to straight.

*Apex.*—Shape. — The stone apex is raised and has an acute, short tip.

*Stone surface.*—Surface Texture. — Irregularly furrowed toward the apex, and pitted toward the base. The stone exhibits substantial pitting laterally. Substantial grooving over the apical shoulders is evident.

Surface pitting is prominent generally, and more frequently, it is present basally. Ridges. — The surface texture varies from sharp to rounded. Ventral Edge. — Width — Considered medium, and having a dimension of approximately 4.0 to 5.0 millimeters at the mid-suture. The wings are most prominent over the suture line. Dorsal Edge. — Shape. — Full, heavily grooved, and having jagged edges. The dorsal edge is moderately eroded over the apical shoulder.

*Stone color.*—The color of the dry stone is a dull red, (approximately RHS Greyed Red Group 180 B).

*Tendency to split.* — Very infrequent splitting was noted.

*Kernel.*—Size. — Length about 16.0 mm.; Width — about 14.0 mm.; Thickness — about 3.0 millimeters. Form. — Obovoid. Pellicle. — Pubescent. Color. — (RHS Greyed Orange Group 166 C).

*Use.*—The subject variety 'Burpeacheleven' is considered to be a Peach tree of the late season maturity, and which produces fruit which are considered very firm, attractively colored, and which are useful for both local and long distance shipping.

*Keeping quality.*—Excellent. Fruit has stored well up to 21 days after harvest at 1.0 degree Celsius.

*Shipping quality.*—Good. Fruit showed minimal bruising of the flesh or skin damage after being subjected to normal harvesting and packing procedures.

*Resistance to insects and disease.*—No particular susceptibilities were noted. The present variety has not been tested to detect for any susceptibilities or resistances to any known plant and/or fruit diseases.

Although the new variety of peach tree possesses the described characteristics when grown under the ecological conditions prevailing near Fowler, Calif., in the Central part of the San Joaquin Valley of California, it should be understood that variations of the usual magnitude and characteristics incident to changes in growing conditions, fertilization, pruning, pest control and horticultural management are to be expected.

Having thus described and illustrated our new variety of peach tree, what we claim is new and desire to secure by Plant Letters Patent is:

1. A new distinct variety of peach tree substantially as illustrated and described, and which is characterized principally as to novelty by producing an attractively colored yellow-fleshed, sub-acid clingstone peach which is mature for harvesting and shipment approximately August 22 to August 31 under the ecological conditions prevailing in the San Joaquin Valley of Central California.

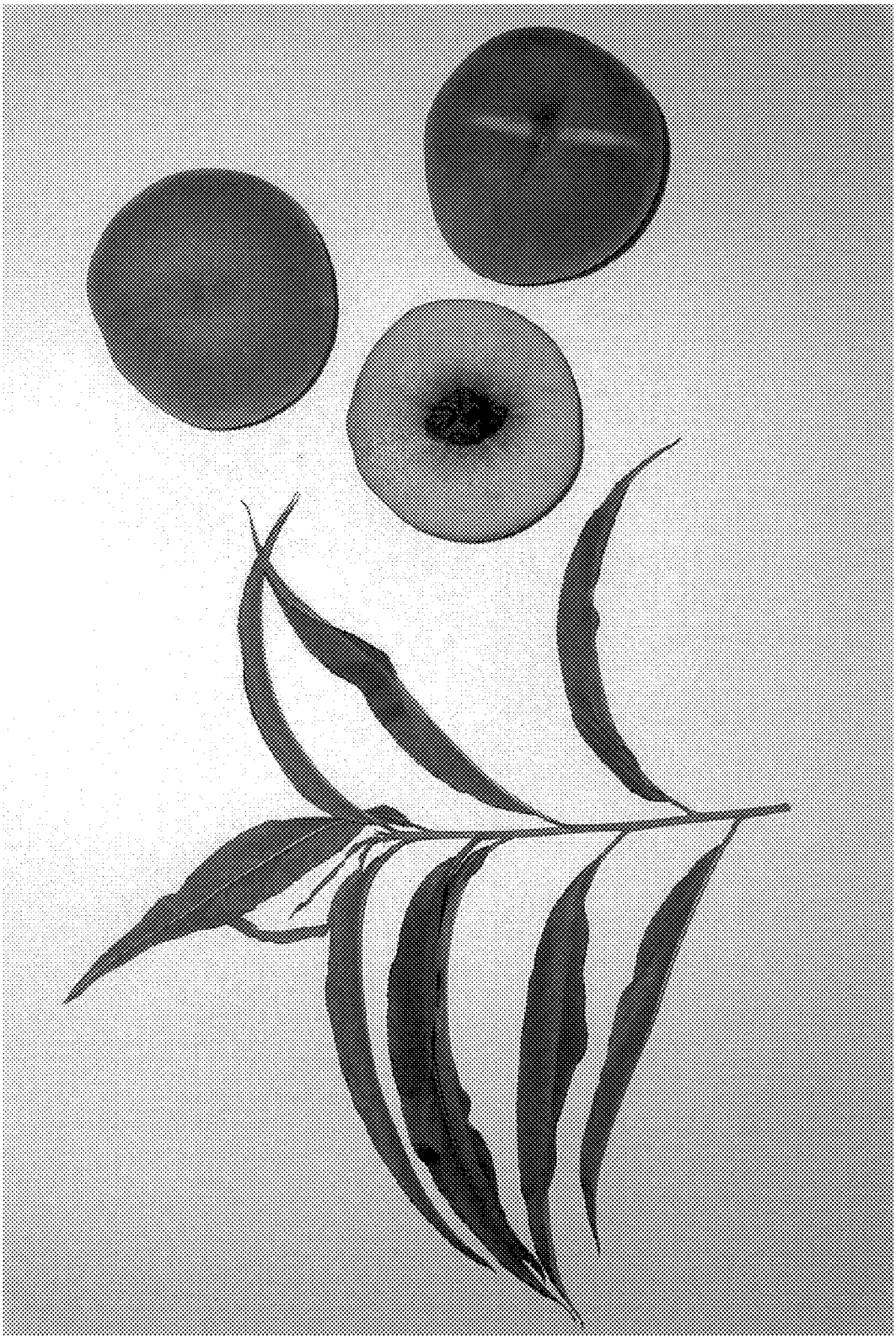

* * * * *